US010028933B2

(12) United States Patent
Kopp et al.

(10) Patent No.: US 10,028,933 B2
(45) Date of Patent: Jul. 24, 2018

(54) COMPOSITIONS AND METHODS FOR INHIBITING THE GROWTH OF MULTI-DRUG RESISTANT MICROBES

(71) Applicant: Ohio State Innovation Foundation, Columbus, OH (US)

(72) Inventors: Benjamin Kopp, Columbus, OH (US); Larry Schlesinger, Powell, OH (US)

(73) Assignee: OHIO STATE INNOVATION FOUNDATION, Columbus, OH (US)

(*) Notice: Subject to any disclaimer, the term of this patent is extended or adjusted under 35 U.S.C. 154(b) by 35 days.

(21) Appl. No.: 15/214,781

(22) Filed: Jul. 20, 2016

(65) Prior Publication Data

US 2017/0020846 A1 Jan. 26, 2017

Related U.S. Application Data

(60) Provisional application No. 62/195,335, filed on Jul. 22, 2015.

(51) Int. Cl.
| | | |
|---|---|---|
| *A61K 31/415* | (2006.01) |
| *C07D 231/12* | (2006.01) |
| *A61K 31/43* | (2006.01) |
| *A61K 31/7036* | (2006.01) |
| *A61K 45/06* | (2006.01) |
| *A61K 31/407* | (2006.01) |
| *A61K 31/5377* | (2006.01) |
| *A61K 31/546* | (2006.01) |

(52) U.S. Cl.
CPC .......... *A61K 31/415* (2013.01); *A61K 31/407* (2013.01); *A61K 31/43* (2013.01); *A61K 31/5377* (2013.01); *A61K 31/546* (2013.01); *A61K 31/7036* (2013.01); *A61K 45/06* (2013.01); *C07D 231/12* (2013.01)

(58) Field of Classification Search
None
See application file for complete search history.

(56) References Cited

U.S. PATENT DOCUMENTS

| 2013/0289004 | A1 | 10/2013 | Chen et al. | |
| 2014/0329777 | A1* | 11/2014 | Morici | A61K 31/63 514/154 |

FOREIGN PATENT DOCUMENTS

WO 2014022382 A2 2/2014

OTHER PUBLICATIONS

Drevinek et al., "Burkholderia cenocepacia in cystic fibrosis: epidemiology and molecular mechanisms of virulence" Clin Microbiol Infect 2010; 16: 821-830 (Year: 2010).*

Hoang et al., "AR-13, a Celecoxib Derivative, Directly Kills Francisella In Vitro and Aids Clearance and Mouse Survival In Vivo" Frontiers in Microbiology (2017) vol. 8 pp. 1-11 (Year: 2017).*
Zhu et al., "From the Cyclooxygenase-2 Inhibitor Celecoxib to a Novel Class of 3-Phosphoinositide-Dependent Protein Kinase-1 Inhibitors" Cancer Research (2004) vol. 64 pp. 4309-4318 (Year: 2004).*
Booth, et al., "Regulation of OSU-03012 toxicity by ER stress proteins and ER stress inducing drugs." Mol Cancer Ther. Oct. 2014; 13 (10): 2384-2398.
Chabrier-Rosello, et al., "Cryptococcus neoformans Phosphoinositide-Dependent Kinase 1 (PDK1) Ortholog is Required for Stress Tolerance and Survival in Murine Phagocytes." Eukaryot Cell. Jan. 2013; 12 (1): 12-22.
Baxter, et al., "Identification, in vitro activity and mode of action of Phosphoinositide-dependent-1 kinase inhibitors as antifungal molecules." ACS Chem Biol. May 11, 2011; 6 (5): 502-510.
Chiu, et al., "Eradication of Intracellular *Salmonella enterica* Serovar Typhimurium with a Small-Molecule, Host Cell-Directed Agent", Antimicrobial Agents and Chemotherapy. Dec. 2009; 53 (12): 5236-5244.
Chiu, et al., "Pharmacological Exploitation of an Off-Target Antibacterial Effect of the Cyclooxygenase-2 Inhibitor Celecoxib against Francisella tularensis," Antimicrobial Agents and Chemotherapy. Jul. 2009; 53 (7): 2998-3002.
Rinehardt, et al., "AR-13 as a potential new therapeutic for reducing antibiotic resistant bacterial burden in cystic fibrosis," Nationwide Children's Hospital and The Ohio State University College of Medicine poster advertisement. Jul. 2016.
Hanulik et al., "An outbreak of Burkholderia multivorans beyond cystic fibrosis patients," Journal of Hospital Infection. Jul. 2013; vol. 84, No. 3, pp. 248-251.
Booth et al., "OSU-03012 and Viagra Treatment Inhibits the Activity of Multiple Chaperone Proteins and Disrupts the Blood-Brain Barrier: Implications for Anti-Cancer Therapies," Journal of Cellular Physiology, Aug. 2015, vol. 230, No. 8, pp. 1982-1998.
Yoo, et al., "Release of cystic fibrosis airway inflammatory markers from Pseudomonas aeruginosa-stimulated human neutrophils involves NADPH oxidase-dependent extracellular DNA trap formation," J Immunol., May 15, 2014, vol. 192, No. 10, pp. 4728-4738.
International Search Report and Written Opinion of PCT Application No. PCT/US2016/043111 dated Sep. 28, 2016.
El-Halfawy et al., "Novel antibiotic combinations proposed for treatment of Burkholderia cepacia complex infections", Antimicrobial Resistance and Infection Control, Nov. 25, 2017, vol. 6(120), pp. 1-5.
Filkins et al., "Cystic Fibrosis Lung Infections: Polymicrobial, Complex, and Hard to Treat", PLOS Pathogens, Dec. 31, 2015, pp. 1-8.
Hiramatsu et al., "Multi-drug-resistant *Staphylococcus aureus* and future chemotherapy", J Infect Chemother, Oct. 2014, vol. 20(10), pp. 593-601.
Koselny et al., "Antitumor/Antifungal Celecoxib Derivative AR-12 is a Non-Nucleoside Inhibitor of the ANL-Family Adenylating Enzyme Acetyl CoA Synthetase", ACS Infect Dis., Apr. 8, 2016, vol. 2(4), pp. 268-280.
Pai et al., "Tuberculosis", Nat Rev Dis Primers, Oct. 27, 2016, vol. 2, pp. 1-23.
Zemanick et al., "Cystic Fibrosis: Microbiology and Host Response", Pediatr Clin North Am, Aug. 2016, vol. 63(4), pp. 617-636.

* cited by examiner

*Primary Examiner* — Eric Olson
(74) *Attorney, Agent, or Firm* — Potomac Law Group, PLLC; Jeremy A. Cubert, Esq.

(57) ABSTRACT

Compositions and methods for preventing and treating infection with multi-drug resistant bacteria with AR-13 alone or in combination with antibiotics are provided.

14 Claims, 15 Drawing Sheets

COMPOSITIONS AND METHODS FOR INHIBITING THE GROWTH OF MULTI-DRUG RESISTANT MICROBES

This application claims priority to U.S. Provisional Patent Application Ser. No. 62/195,335, filed Jul. 22, 2015. The above referenced application is incorporated herein by reference as if restated in full.

BACKGROUND

There are no known effective treatments for *Burkholderia cenocepacia* (*B. cenocepacia* or Bc) infections in patients with cystic fibrosis (CF) due to extensive multi-drug resistance (antibiotic resistance) of the bacteria and decreased ability of the immune cells of patients with CF to kill the bacteria. We have demonstrated that defective bacterial killing in patients with CF is caused, in part, by deficient autophagy in immune effector cells such as macrophages. *B. cenocepacia* is the most problematic and feared pathogenic organism in patients with CF, causing Cepacia syndrome, sepsis, and rapid spread of the bacteria in the infected patient.

Currently, no effective treatments are available for the treatment of *B. cenocepacia* infections in patients with CF due in part to the resistance to multiple antibiotics by the bacteria. *B. cenocepacia* infection in CF is a contraindication to life-sustaining lung transplant due to poor survival of infected patients. Immunocompromised patients (e.g., chronic granulomatous disease, ICU patients) are also susceptible to *Burkholderia* infections. Recent *Burkholderia* outbreaks in non-CF populations have been extremely virulent. Overall, one in four patients with *Burkholderia* infections die, and one out of every three patients infected with *Burkholderia* in the ICU setting die. Hanulik et al., An outbreak of *Burkholderia multivorans* beyond cystic fibrosis patients. J Hosp Infect. 2013 July; 84(3):248-51. PMID: 23706672.

Available treatments for *Pseudomonas aeruginosa* are limited due to acquired antibiotic resistance (e.g., hospital-acquired infections). *P. aeurginosa* infections are common in patients with CF and can cause chronic, persistent infections with long-term morbidity and mortality. In addition, *P. aeruginosa* multi-drug resistance develops over time with continued antibiotic exposure, as the antibiotic treatment intended to clear the chronic *P. aeruginosa* infection contributes to the development of antibiotic resistance.

*P. aeruginosa* infections can be treated by a variety of antibiotics including aminoglycosides, fluoroquinolones, and advanced generation cephalosporins, but treatment with these antibiotics drugs has led to further and extensive drug resistance by the bacteria.

Previously, the celecoxib derived chemical agent AR-12 (a.k.a. OSU-03012), which is an analogue of AR-13, exhibited antibacterial activity against the intracellular bacteria *Salmonella Typhimurium* and *Francisella tularensis* in macrophages. AR-12 is an orally bioavailable small molecule with substantial anti-bacterial activity across multiple bacterial pathogens including, for example, *Salmonella* and *Francisella*.

AR-12 is a celecoxib derivative that was discovered at The Ohio State University. The compound was initially developed in the oncology setting and a phase I study demonstrated an acceptable safety profile with long term oral exposures up to 33 weeks. The AR-12 oncology dose most likely substantially exceeds the exposure needed in the infectious disease setting. AR-12 has been previously shown to exhibit anti-tumor and anti-bacterial activity. It is thought that AR-12 induces autophagy of cells harboring intracellular bacteria. Supportive preclinical studies demonstrated that AR-12 has rapid blood brain barrier penetration and appreciable accumulation in tissues, exceeding the blood level concentrations by several fold. Booth L, Roberts J L, Tavallai M, Nourbakhsh A, Chuckalovcak J, Carter J, Poklepovic A, Dent P. OSU-03012 and Viagra Treatment Inhibits the Activity of Multiple Chaperone Proteins and Disrupts the Blood-Brain Barrier: Implications for Anti-Cancer Therapies. J Cell Physiol. 2015 August; 230(8):1982-98. doi: 10.1002/jcp.24977. PubMed PMID: 25736380.

AR-13, an AR-12 analog, has also been shown to have antibacterial activity. See e.g., U.S. Patent Application Publication 2013/0289004.

SUMMARY

Aspects described herein provide compositions and methods for reducing the bacterial load in a host. In another aspect, the microbes are multi-drug resistant bacteria. In one aspect, the multi-drug resistant bacteria are selected from the group consisting of *B. cenocepacia* and *P. aeruginosa*. In another aspect the composition comprises AR-13 and a broad-spectrum antibiotic. The combination of AR-13 and a broad-spectrum antibiotic can, for example, reduce the load of microbes in a synergistic manner.

As described herein, the combination of AR-13 and antibiotics decreases the load of bacteria in infected macrophages and neutrophils in a synergistic manner compared to that of AR-13 or the antibiotic alone. Administering the combination of AR-13 and broad-spectrum antibiotics is a therapeutic strategy for controlling bacterial infections which are resistant to standard antibiotics in patients with CF.

One aspect provides compositions for inhibiting bacterial growth comprising AR-13 and an antibiotic. In another aspect, the antibiotic is selected from the group consisting of cephalosporins, quinolones, aminoglycosides, and carbapenems. In yet another aspect, the antibiotic is selected from the group consisting of ceftazidime, ciprofloxacin, gentamicin, and meropenem.

In another aspect, the compositions further comprise a pharmaceutical carrier.

In yet further aspects, AR-13 is provided in an amount to achieve a blood or tissue concentration of at least about 2.5 µM.

In another aspect, the antibiotic is provided in an amount to achieve a peak blood or tissue concentration of at least about 5 µg/ml.

In another aspect, the compositions further comprise at least a second antibiotic (e.g., cephalosporins, quinolones, aminoglycosides, carbapenems).

Further aspects provide methods of reducing the load of microbes in a host by administering AR-13 and an antibiotic to the host wherein the load of the microbes is reduced by about 1000 fold.

In another aspect, the microbes are selected from the group consisting of *P. aeruginosa* and *B. cenocepacia*.

In yet another aspect, AR-13 is administered to the host in an amount sufficient to achieve a blood or tissue concentration of at least 2.5 µM.

In a further aspect, the broad-spectrum antibiotic is administered to the host in an amount sufficient to achieve a peak blood or tissue concentration at least about 5 µg/ml.

Another aspect provides methods of reducing the load of *P. aeruginosa* infected human neutrophils in a host, comprising administering AR-13 and an antibiotic to the host wherein the load of the bacteria in human neutrophils is reduced by about 4 fold.

Yet another aspect provides methods of reducing the load of *B. cenocepacia* infected human macrophages from patients with CF in a host by administering AR-13 and an antibiotic to the host wherein the load of the bacteria in macrophages from patients with CF is reduced by about 1000 fold.

BRIEF DESCRIPTION OF THE DRAWINGS

The feature and nature of the present disclosure will become more apparent from the detailed description set forth below when taken in conjunction with the accompanying drawings.

FIG. 1A shows the exemplary optical absorbance density of bacteria over a 24 hour period for *B. cenocepacia* alone and treated as indicated;

FIG. 1B is an endpoint analysis of the experimental results shown in FIG. 1A;

FIG. 1C is an endpoint analysis of bacterial density at 24 hours for *B. cenocepacia* alone and treated as indicated with AR-13 and AR-13 plus an antibiotic;

FIG. 1D shows the exemplary 24 hour bacterial killing assay of CF clinical MRSA isolate treated with antibiotics alone or with antibiotics plus AR-13 as indicated;

FIG. 1E is a 24 hour endpoint analysis of the experimental results shown in FIG. 1D;

FIG. 1F shows an exemplary end-point analysis of bacterial density of MRSA in response to the dose titration of AR-13;

FIG. 1G shows the results of an exemplary bacterial killing assay of CF clinical *P. aeruginosa* isolate with antibiotics alone or antibiotics plus AR-13 as indicated;

FIG. 1H is a 24 hour endpoint analysis of the experimental results shown in FIG. 1G;

FIG. 2A shows an exemplary 24 hour CFU assay of human CF and non-CF monocyte-derived macrophages (MDMs) infected with *B. cenocepacia* and treated with or without AR-13;

FIG. 2B shows an exemplary 24 hour CFU assay of human CF MDMs infected with *B. cenocepacia* and treated with antibiotics alone or with AR-13;

FIG. 2C shows an exemplary 24 hour CFU assay of human CF and non-CF neutrophils infected with MRSA with and without AR-13;

FIG. 2D shows an exemplary 24 hour CFU assay of human CF neutrophils infected with MRSA and treated with antibiotics alone or with AR-13;

FIG. 2E shows an exemplary 24 hour CFU of human CF and non-CF neutrophils infected with *P. aeruginosa* and treated with and without AR-13;

FIG. 2F shows an exemplary 24 hour CFU assay of human CF neutrophils infected with *P. aeruginosa* and treated with antibiotics alone or antibiotics plus AR-13; and FIG. 3 shows an exemplary macrophage viability assay at 24 h for human CF and non-CF MDMs without infection (NT), with infection with *B. cenocepacia* (Bc), with treatment with AR-13 (AR-13), or infection plus treatment with AR-13 (Bc+AR-13).

DETAILED DESCRIPTION

The disclosed methods, compositions, and devices below may be described both generally as well as specifically. It should be noted that when the description is specific to an aspect, that aspect should in no way limit the scope of the methods.

In one aspect, compounds suitable for use alone or in combination with antibiotics as described herein include, for example, AR-13 (N-{4-[5-(Phenanthren-2-yl)-3-(trifluoromethyl)-1H-pyrazol-1-yl]phenyl}sulfuric diamide), having the following structure:

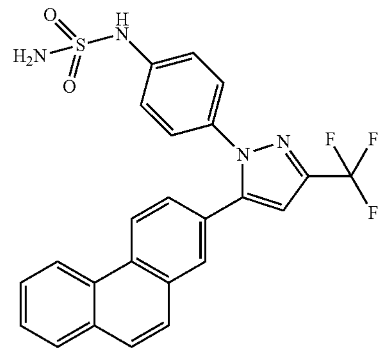

Antibiotic resistance is an increasing medical and public health problem, especially in the hospital environment. Immune-compromised patients or individuals with underlying diabetes mellitus, cardiovascular or pulmonary disorders exposed to antibiotic resistant strains of bacteria are particularly at risk. Patients with cystic fibrosis are especially susceptible to pulmonary infections secondary to multiple factors including: altered lung function, inability to clear viscous, purulent sputum, and an intrinsic inability of the macrophages and other immune effector cells to effectively kill intracellular bacteria. Infections in the upper and lower airways of patients with CF are commonly polymicrobial resulting in biofilms which once established are difficult to eradicate with current treatments and available antibiotics. Patients with CF, in particular, are at risk for infections with *B. cenocepacia* and *P. aeruginosa. B. cenocepacia* has underlying intrinsic antibiotic resistance while *P. aeruginosa* develops resistance through exposure to antibiotics. The clinical effectiveness and success of the antibiotics commonly used to treat these infections in patients with CF depends on the bacteria present and the individual antibiotic susceptibility profile of the infectious bacteria.

One aspect provides compositions for inhibiting microbial growth comprising AR-13 and an antibiotic. The composition can be provided to a patient infected with a microbe or as preventative measure to reduce the risk of patients at high risk for serious infections (e.g., patients with CF or immunocompromised patients).

The effectiveness of treatment with the compositions provided herein can be measured by assessing the load of the microbe (e.g., bacteria) of interest, for example, in macrophages or neutrophils. For example, bacterial loads can be measured in cells with and without treatment with the compositions provided herein, and measured over desired intervals (hourly, daily, weekly etc.) and the bacterial load between treated and untreated cells for a desired interval can be compared to determine the fold decrease in bacterial load. In one aspect, the bacterial load in macrophages is reduced by at least about 1000 fold.

In another aspect, the antibiotic is selected from the group consisting of cephalosporins, fluoroquinolones, aminoglycosides, and carbapenems. In another aspect, the antibiotic is selected from the group consisting of ceftazidime, ciprofloxacin, gentamicin, and meropenem.

The compositions further comprise a pharmaceutical carrier which can be combined in a suitable manner with AR-13 and an antibiotic to, for example, facilitate administration of the composition to a patient and delivery of the drug to the site of infection. Pharmaceutical carriers include, but are not limited to, creams, gels, solutions, suspensions (including, but not limited to liposomal suspensions), solid dosage forms, emulsions, or the like.

The relative dose of AR-13 and the antibiotic can be adjusted to further limit the risk of developing antibiotic resistance. In one aspect, AR-13 is provided in an amount to achieve a blood or tissue concentration of at least about 2.5 µM and the antibiotic is provided in an amount to achieve a blood or tissue concentration of at least about 5 µg/ml.

The compositions provided herein can further comprise a second antibiotic to treat patients who are also afflicted with secondary infections.

Microbes susceptible to treatment with the compositions described herein include, but are not limited to P. aeruginosa, and B. cenocepacia. In another aspect, the bacteria are multi-drug resistant.

Further methods of administering AR-13 and an antibiotic can reduce the titer of B. cenocepacia infected human CF macrophages by about 1000 fold. As shown in FIGS. 1A and 1B, AR-13 alone has direct killing effect on B. cenocepacia in media alone. FIG. 1 illustrates that the optical density of B. cenocepacia in media alone changes significantly after providing AR-13 at a concentration of 5 µM.

The bacteria were grown in luria-bertani (LB) broth for 24 hours at 37° C. and then added to RPMI media in 96 well microtiter plates. Varying concentrations of AR-13 from 5-20 µg/ml were then added to the wells in triplicate and the optical absorbance reading of bacterial growth was taken over a 24 hour period and compared between RPMI (media) alone, bacteria alone, and bacteria plus AR-13.

The combination of AR-13 and ceftazidime, or ciprofloxacin, or gentamicin, or meropenem reduces the colony forming units (CFU)/ml in CF macrophages by at least 1000 fold as shown in FIG. 2. In this aspect, human CF monocytes were separated from peripheral blood samples using a Ficol gradient via Lymphocyte Separation Medium (Corning, 25-072-CV). Isolated monocytes were re-suspended in RPMI (Gibco, 22400-089) and 10% human AB serum (Lonza, 14-490E) to a concentration of $2 \times 10^6$ cells/mL and incubated for 5 days at 37° C. to derive macrophages. Macrophages were then adhered to microtiter plates and infected with B. cenocepacia strain k56-2 at a multiplicity of infection (MOI) of 10 over the stated times. Antibiotics or antibiotics plus AR-13 were then added to wells for 24 hours. For colony forming unit analysis, in order to enumerate intracellular bacteria, infected macrophages were lysed with ice-cold PBS (Invitrogen, 14190) after 24 hours. Recovered bacteria were quantified by plating serial dilutions on LB agar plates and counting colonies using the Acolyte Colony Counter, 5710/SYN.

Aspects described herein provide methods of reducing the titer of P. aeruginosa infected human neutrophils in a host. In this aspect, human neutrophils are isolated from peripheral blood samples and immediately processed into tissue culture. Neutrophils are infected with P. aeruginosa for 2 hours prior to treatment with AR-13 for 4-24 hours. Neutrophil isolation from patients with CF has been described previously. Yoo et al., Release of cystic fibrosis airway inflammatory markers from Pseudomonas aeruginosa-stimulated human neutrophils involves NADPH oxidase-dependent extracellular DNA trap formation. J Immunol. 2014 May 15; 192(10):4728-38. PubMed PMID: 24740504;

AR-13 has a direct killing effect against B. cenocepacia. FIG. 1A is a screening bacterial killing assay of AR-12, AR-13, derivatives thereof and other test compounds for direct killing against B. cenocepacia.

As shown in FIG. 1A, AR-13 alone reduces the optical absorbance density of B. cenocepacia by about 1.3 fold compared to no treatment (B. cenocepacia alone) indicating a direct killing effect on B. cenocepacia. Optical density was measured over a 24 hour period (n=3).

FIG. 1B also shows a reduction in optical absorbance by about 1.3 fold compared to no treatment (B. cenocepacia alone).

Figure 1A:
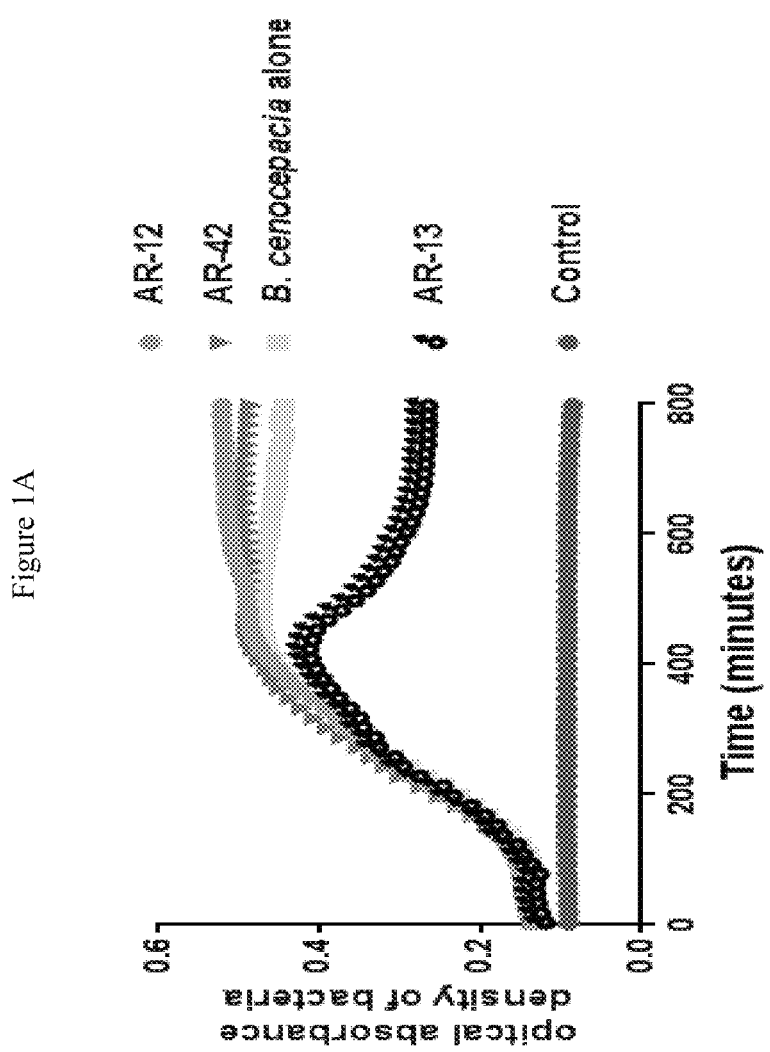
FIG. 1B is an endpoint analysis of bacterial density at 24 hours for the experiment of FIG. 1A.
FIG. 1C is an endpoint analysis of bacterial density at 24 hours of B. cenocepacia with antibiotics (ceftazidime, ciprofloxacin, gentamicin, and meropenem) or antibiotics and AR-13 over a 24 hour period (n=3).
Figure 1B:
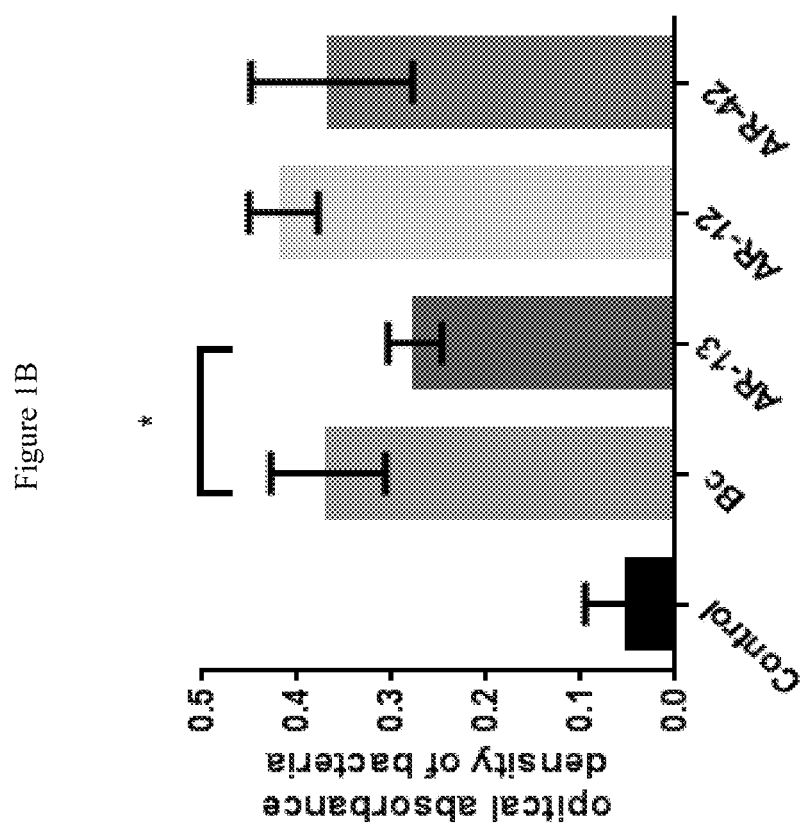
Figure 1C:
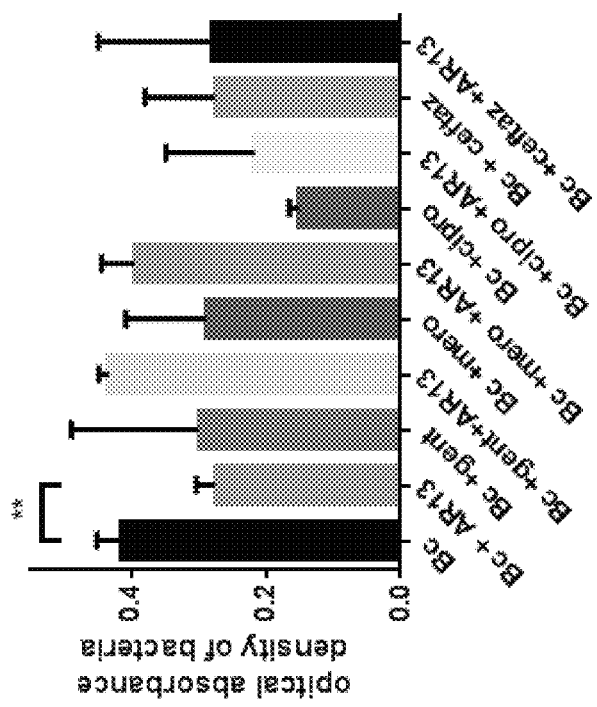
Figure 1D:
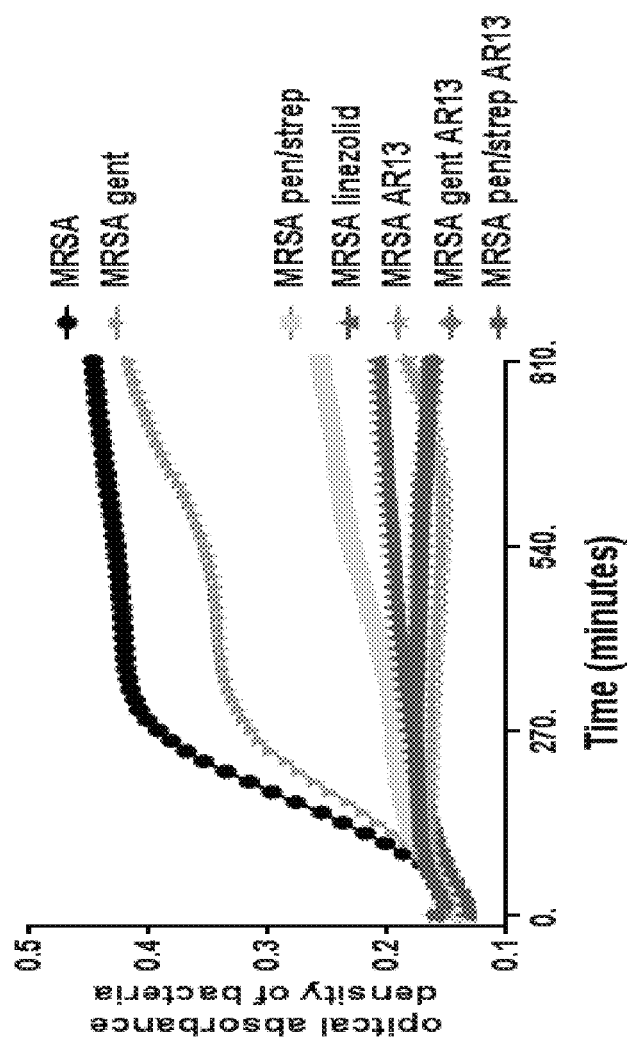

FIG. 1D shows the results of a bacterial killing assay of MRSA isolated from a patient with CF treated with antibiotics alone or antibiotics (penicillin, streptomycin, linezolid) and AR-13 over a 24 hour period (n=3). As shown in FIG. 1D, combinations of antibiotics and AR-13 reduced the optical absorbance density of MRSA by about 2.5 fold compared to no treatment and by about 2 fold compared to antibiotics alone. AR-13 alone reduced the optical absorbance density of MRSA by about 1.3 fold compared to no treatment.

Figure 1E:
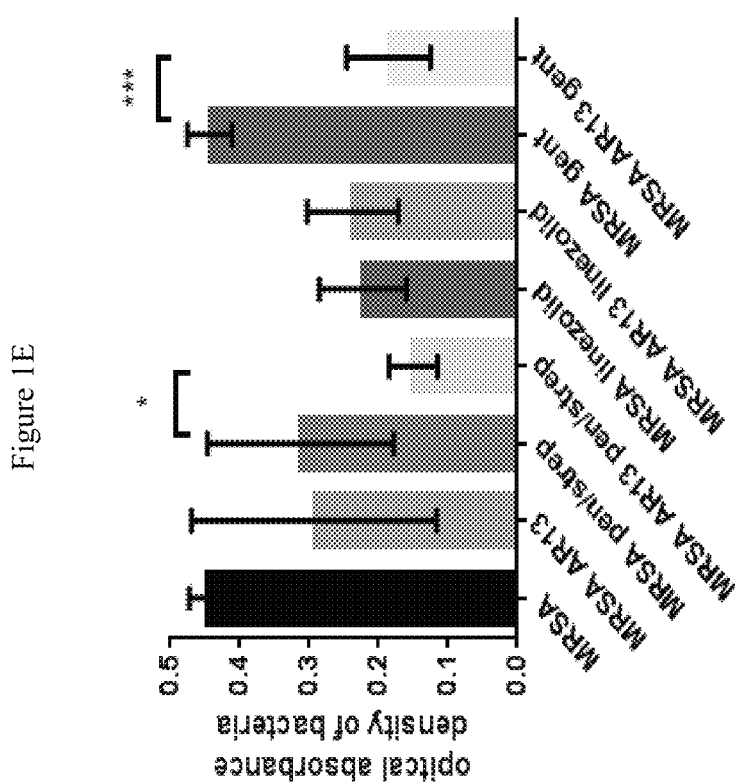

FIG. 1E is an endpoint analysis of bacterial density at 24 hours for the experiment of FIG. 1D.

Figure 1F:
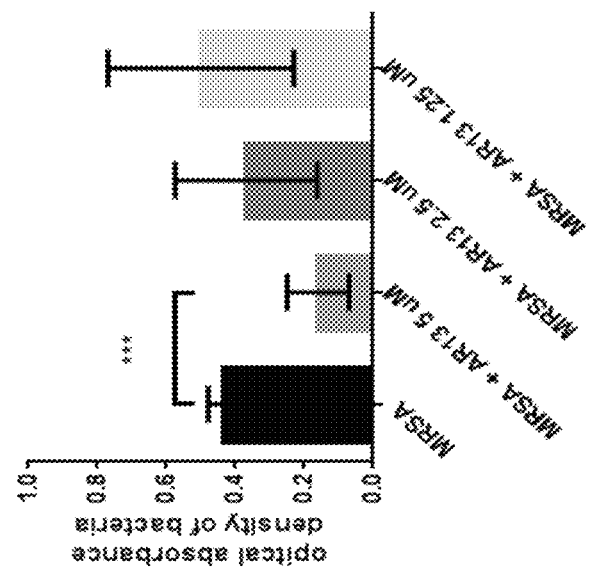

FIG. 1F shows an endpoint analysis of bacterial density of MRSA in response to dose titration of AR-13 at 24 hours (n=3). As shown in FIG. 1F, bacterial optical density increases as the dose of AR-13 decreases from 5 to 2.5 to 1.25 µM.

Figure 1G:
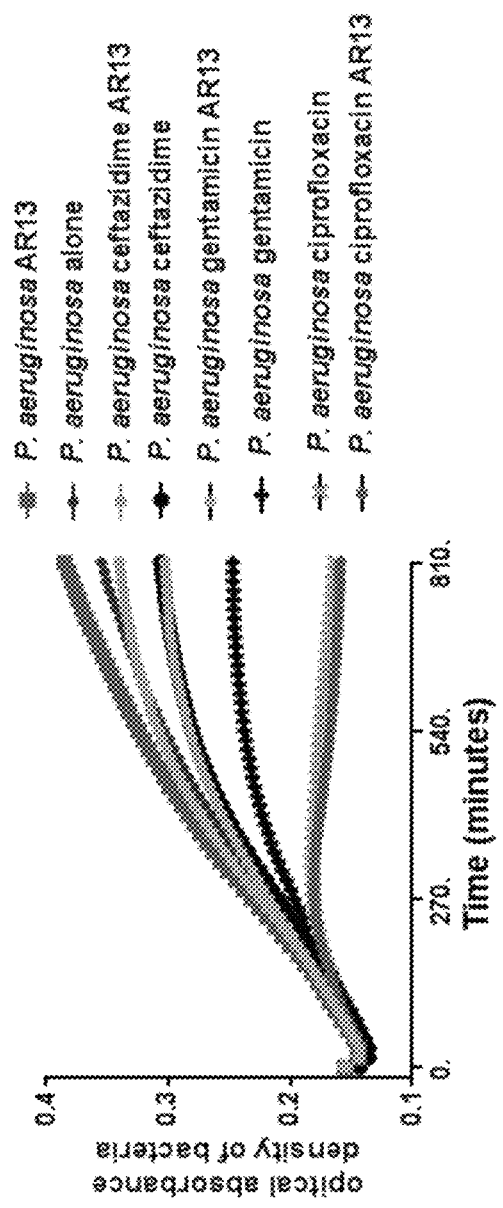

FIG. 1G shows the results of a 24 hour (n=3) direct bacterial killing assay in media alone for P. aeruginosa (isolated from a patient with CF) with antibiotics (gentamycin, ciprofloxacin, and ceftazidime) alone and with AR-13. As shown in FIG. 1G, the addition of AR-13 alone or in combination with antibiotics did not enhance bacterial killing in media.

Figure 1H:
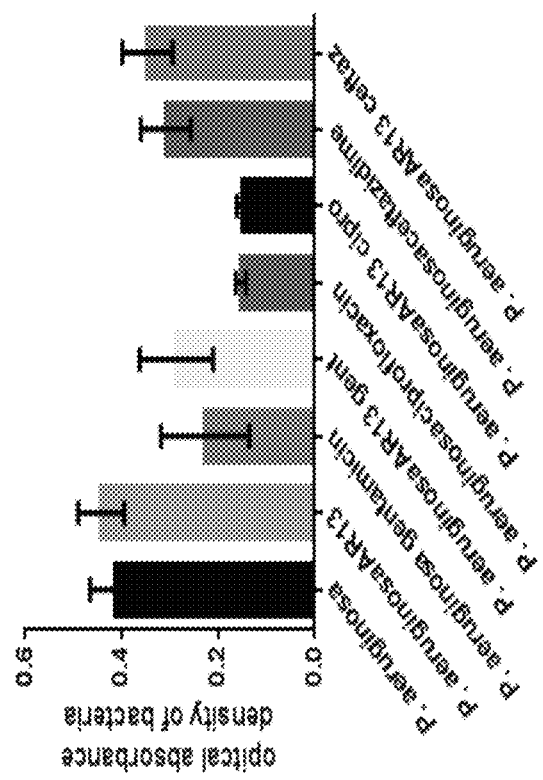

FIG. 1H shows an endpoint analysis of bacterial density for the experiment of FIG. 1G.

For FIGS. 1A-1H, "*"=P value<0.05, "*"=P value<0.01, "***"=P value<0.001.

FIG. 2 shows the results of a 24 hour colony forming unit (CFU) assay of human CF and non-CF monocyte-derived macrophages infected with B. cenocepacia (Bc)±treatment with AR-13 (n=3).

Figure 2A:
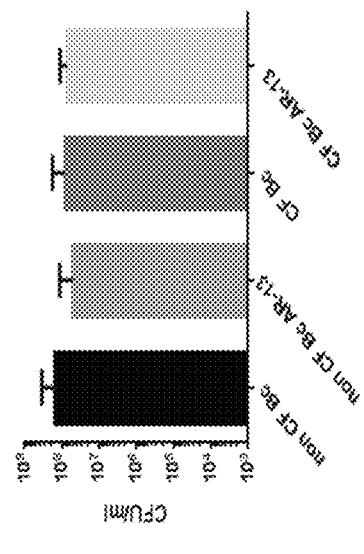
Figure 2B:
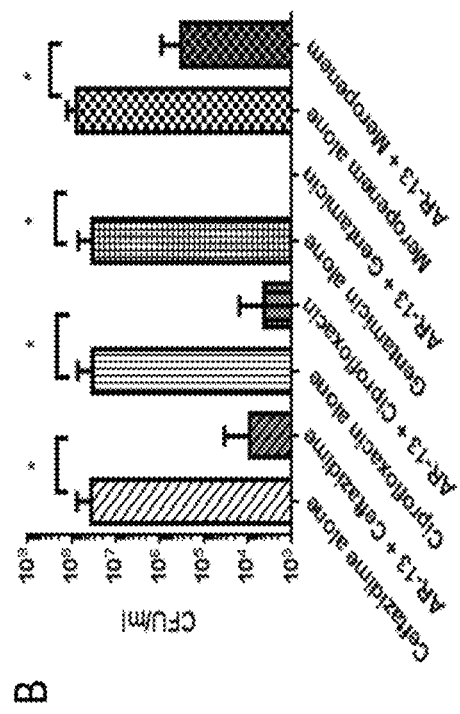

As shown in FIG. 2A, AR-13 had no effect on the CFU/ml for non CF or CF human monocyte-derived macrophages (MDM) infected with B. cenocepacia. However, as shown in FIG. 2B, the CFU/ml was reduced by about 10000 fold in human CF MDMs infected with Bc and treated with AR-13 plus ceftazidime, AR-13 plus ciprofloxacin, AR-13 plus gentamicin, and AR-13 plus meropenem.

Figure 2C:
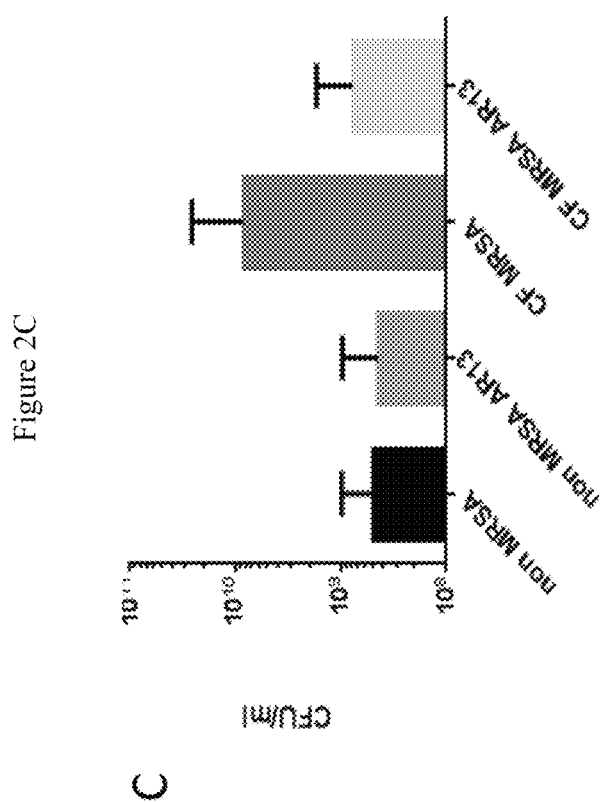

As shown in FIG. 2C, AR-13 had no effect in a 24 hour CFU assay of human CF and non-CF MDMs infected with MRSA and treated with and without AR-13.

Figure 2D:
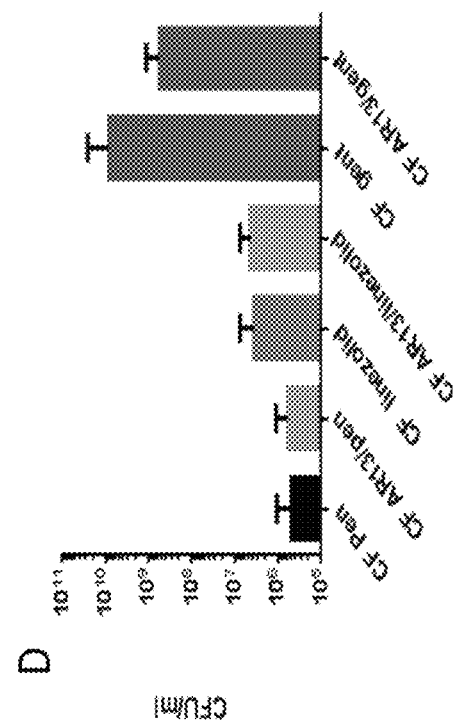

Similarly, as shown in FIG. 2D, AR-13 alone or in combination with antibiotics had no effect in a 24 hour CFU assay of non CF or CF human MDMs infected with MRSA (n=2).

Figure 2E:
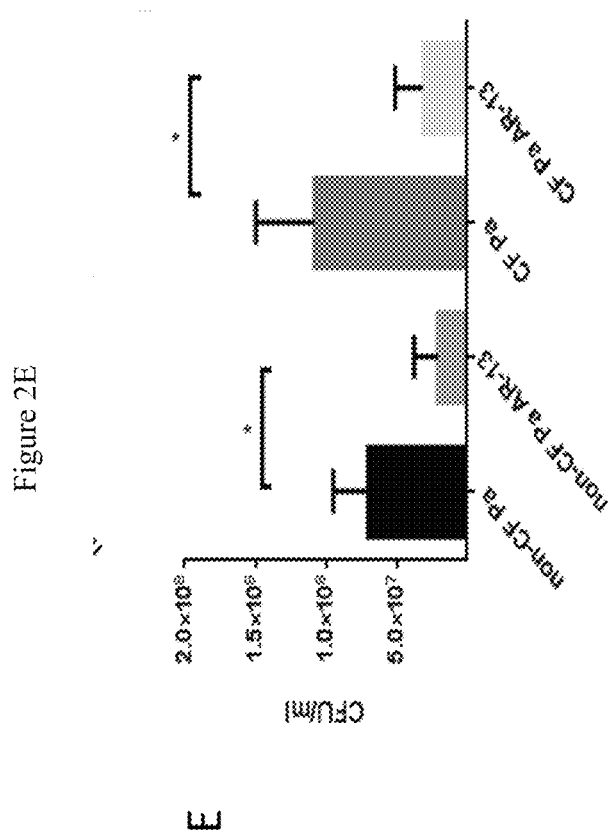
Figure 2F:
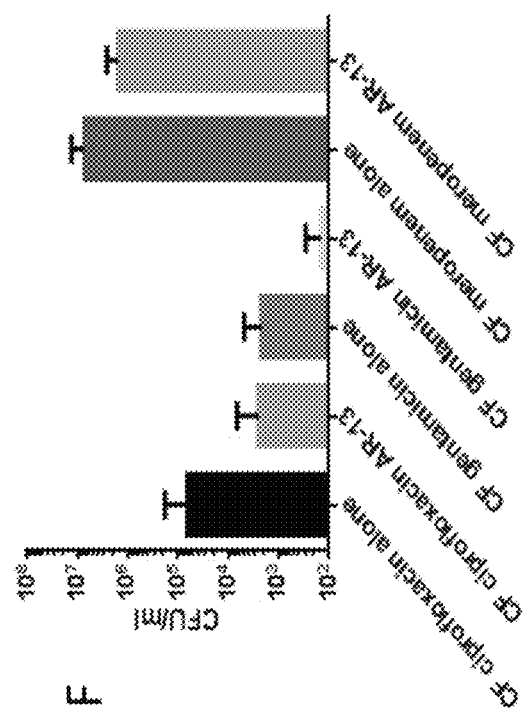

In contrast, as shown in FIG. 2E, AR-13 reduced the CFU/ml by about 10 fold in a 24 hour CFU assay of human CF and non-CF neutrophils infected with *P. aeruginosa* (Pa), (n=3). As shown in FIG. 2F, human CF neutrophils infected with *P. aeruginosa* and treated with antibiotics alone showed no difference in CFU/ml compared to treatment with antibiotics plus AR-13 (24 hours, n=3).

For FIGS. 2A-2F, "*"=P value<0.05, ""=P value<0.01, "*"=P value<0.001.

Figure 3:
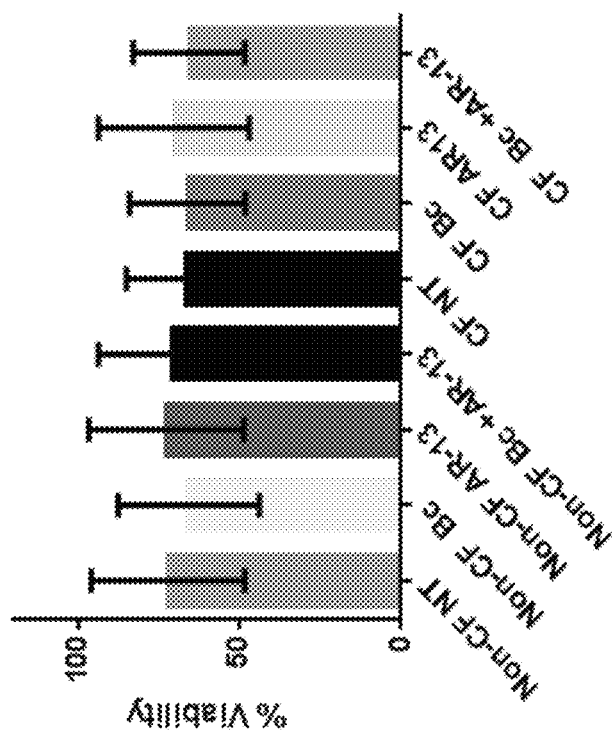

FIG. 3 shows that AR-13 does not impact macrophage viability in human MDMs infected with *B. cenocepacia* (Bc) or uninfected MDMs.

As discussed herein, in one aspect, AR-13 had no direct effect on *P. aeruginosa* growth in media devoid of human macrophages or neutrophils. In this aspect, there was a 23% reduction in *B. cenocepacia* burden in infected CF and non-CF macrophages using 5 µM AR-13 alone; in contrast, there was a 70% reduction in *P. aeruginosa* burden in CF neutrophils and 66% reduction in non-CF neutrophils using AR-13 alone.

AR-13 in combination with gentamicin, ciprofloxacin or ceftazidime caused a significant synergistic reduction in *B. cenocepacia* burden in CF macrophages, and a modest reduction in conjunction with meropenem (FIG. 2). Antibiotics alone had no reduction in *B. cenocepacia* burden in CF macrophages in contrast to non-CF macrophages, but did reduce *P. aeruginosa* burden in both CF and non-CF neutrophils. CF and non-CF macrophages and neutrophils tolerated AR-13 in concentrations up to 10 µM, with increased macrophage viability as noted in the CF macrophages compared to antibiotics alone. In another aspect, AR-13 concentrations above about 10 µM resulted in increased toxicity in uninfected MDMs.

In yet another aspect, AR-13, in combination with antibiotics with broad spectrum antimicrobial activity, has a synergistic effect on reducing antibiotic-resistant *B. cenocepacia* burden in human CF macrophages. In a further aspect, AR-13 alone significantly reduces *P. aeruginosa* burden in CF neutrophils. AR-13 can be used as a new therapeutic option for patients acutely and chronically infected with *B. cenocepacia* and other antibiotic resistant microorganisms, for which there are no currently available therapies or for which the available therapies have limited therapeutic efficacy.

In another aspect, AR-13 or the compositions described herein can be used to treat or prevent the illness and/or disease caused by infectious microbes including, but not limited to, those listed above. AR-13 can be provided to an infected patient concurrently with an antibiotic or serially in any suitable order. In another aspect, AR-13 and the antibiotic can be administered to patients simultaneously or AR-13 and the antibiotic can be formulated together.

The term "administer" or "administer" refers to providing the compositions described herein to a patient including by the patient, a healthcare professional, a caretaker, and also includes prescribing the compositions described herein to the patient.

The compositions described herein can be administered orally, parenterally (intravenously [IV], intramuscularly [IM], depot-IM, subcutaneously [SQ], and depot-SQ), sublingually, intranasally, by inhalation, intrathecally, topically, or rectally. Dosage forms known to those of skill in the art are suitable for delivery of the compositions described herein.

AR-13 can be formulated into suitable pharmaceutical preparations such as creams and gels, for topical application; suspensions, tablets, capsules, or elixirs for oral administration or in sterile solutions or suspensions for parenteral administration, suspensions or solutions appropriate for inhalation (e.g., metered dose inhalers, dry powder inhaler, nanoparticles). AR-13 can be formulated into pharmaceutical compositions using techniques and procedures well known in the art.

In one aspect, about 0.1 to 1000 mg, about 5 to about 200 mg, or about 10 to about 50 mg of the AR-13, or a physiologically acceptable salt or ester can be compounded with a physiologically acceptable vehicle, carrier, excipient, binder, preservative, stabilizer, flavor, etc., in a unit dosage form as called for by accepted pharmaceutical practice. The amount of active substance in compositions or preparations comprising AR-13 is such that a suitable dosage achieving the therapeutic range indicated is obtained.

In another aspect, the compositions can be formulated in a unit dosage form, each dosage containing from about 1 to about 1000 mg, about 1 to about 500 mg, or about 10 to about 200 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

In one aspect, one or more of AR-13 is mixed with a suitable pharmaceutically acceptable carrier to form compositions. Upon mixing or addition of the compound(s), the resulting mixture may be a cream, gel, solution, suspension, emulsion, or the like. Liposomal suspensions may also be used as pharmaceutically acceptable carriers. These may be prepared according to methods known to those skilled in the art. The form of the resulting mixture depends upon a number of factors, including the intended mode of administration and the solubility of the compound in the selected carrier or vehicle. In one aspect, the effective concentration is sufficient for lessening or ameliorating at least one symptom of the disease, disorder, or condition treated and may be empirically determined.

Pharmaceutical carriers or vehicles suitable for administration of AR-13 described herein include any such carriers suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

In another aspect, if AR-13 exhibits insufficient solubility, methods for solubilizing may be used. Such methods are known and include, but are not limited to, using co-solvents such as ethanol (EtOH) or dimethylsulfoxide (DMSO), using surfactants (e.g., anionic, cationic, zwitterionic, and non-ionic). Specific suitable surfactants include, but are not limited to, TWEEN, poloxamer, sodium lauryl sulfate, aluminum monostearate and dissolution in aqueous sodium bicarbonate. Derivatives of the compounds, such as salts or prodrugs, may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration.

In another aspect, AR-13 as described herein may be prepared with carriers that protect them against rapid elimination from the body, such as time-release formulations or coatings. Such carriers include controlled release formulations, such as, but not limited to, microencapsulated delivery systems. The active compound can be included in the pharmaceutically acceptable carrier in an amount sufficient to exert a therapeutically useful effect in the absence of undesirable side effects on the patient treated. The therapeutically effective dose may be determined empirically by testing the compounds in known in vitro and in vivo model systems for the treated disorder.

In another aspect, AR-13 and compositions described herein can be enclosed in multiple or single dose containers. The enclosed compounds and compositions can be provided in kits, for example, including component parts that can be assembled for use. For example, AR-13 in lyophilized form and a suitable diluent may be provided as separated components for combination prior to use. A kit may include AR-13 and a second therapeutic agent for co-administration. AR-13 and second therapeutic agent may be provided as separate component parts. A kit may include a plurality of containers, each container holding one or more unit dose of AR-13 described herein. In one aspect, the containers can be adapted for the desired mode of administration, including, but not limited to suspensions, tablets, gel capsules, sustained-release capsules, and the like for oral administration; depot products, pre-filled syringes, ampoules, vials, and the like for parenteral administration; and patches, medipads, gels, suspensions, creams, and the like for topical administration.

The concentration of AR-13 in the pharmaceutical composition will depend on absorption, inactivation, and excretion rates of the active compound, the dosage schedule, and amount administered as well as other factors known to those of skill in the art.

In another aspect, the active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient (e.g., any suitable filler/bulking agent) such as microcrystalline cellulose, starch, or lactose; a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed or co-administered with other active materials that do not impair the desired action, or with materials that supplement the desired action. AR-13 can be used, for example, in combination with an antibiotic, antiviral, antifungal, pain reliever, or a cosmetic.

In one aspect, solutions or suspensions used for parenteral, intradermal, subcutaneous, inhalation, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, alcohols, polyethylene glycol, glycerin, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include, but are not limited to, physiological saline, phosphate buffered saline (PBS), and solutions containing thickening and solubilizing agents such as glucose, polyethylene glycol, polypropyleneglycol, ethanol, N-methylpyrrolidone, surfactants and mixtures thereof. Liposomal suspensions including tissue-targeted liposomes may also be suitable as pharmaceutically acceptable carriers. These may be prepared according to methods known in the art.

In another aspect, AR-13 may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

In yet another aspect, compounds employed in the methods of the disclosure may be administered enterally or parenterally. When administered orally, compounds employed in the methods of the disclosure can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, they can be of the sustained release type so that the compounds employed in the methods described herein need to be administered only once or twice daily.

The dosage forms can be administered to the patient 1, 2, 3, or 4 times daily. AR-13 as described herein can be administered either three or fewer times, or even once or twice daily.

The terms "therapeutically effective amount" and "therapeutically effective period of time" are used to denote treatments at dosages and for periods of time effective to reduce microbial burden. As noted above, such administration can be parenteral, oral, sublingual, transdermal, topical, intranasal, or intrarectal. In one aspect, when administered systemically, the therapeutic composition can be administered at a sufficient dosage to attain a blood level of the compounds of from about 0.1 µM to about 20 µM. For localized administration, much lower concentrations than this can be effective, and much higher concentrations may be tolerated. One skilled in the art will appreciate that such therapeutic effect resulting in a lower effective concentration of AR-13 may vary considerably depending on the tissue, organ, or the particular animal or patient to be treated. It is also understood that while a patient may be started at one dose, that dose may be varied overtime as the patient's condition changes.

EXAMPLES

Example 1—Materials and Methods

Bacterial Strains

Macrophages were infected with a RFP-expressing *B. cenocepacia* strain k56-2. The *B. cenocepacia* strain is representative of an epidemic clinical strain from the ET12 lineage. Neutrophils were infected with a pan-resistant *P. aeruginosa* isolate and a linezolid sensitive MRSA isolate obtained from the sputum of patients with CF at National Children's Hospital (NCH). Bacteria were reproducibly grown in media over 24 hours. For colony forming unit analysis, 50 µg/ml gentamicin (Invitrogen, 3564) was added for 0.5 hours as described previously. Infected macrophages or neutrophils were lysed with ice-cold PBS (Invitrogen, 14190) after 24 hours and intracellular bacteria enumerated. Bacteria were then quantified by plating serial dilutions on LB agar plates and counted using the Acolyte Colony Counter, 5710/SYN.

Phagocyte Isolation

CF and non-CF healthy controls donated heparinized blood samples. Subjects were excluded if using chronic immunosuppressants, CFTR modulators, or had a history of transplantation. Peripheral monocytes were separated from whole blood using Lymphocyte Separation Medium (Corning, 25-072-CV). Isolated monocytes were re-suspended in RPMI (Gibco, 22400-089) plus 10% human AB serum (Lonza, 14-490E) and differentiated for 5 days at 37° C. into MDMs. MDMs were then placed in a monolayer culture, and infected at bacterial multiplicity of infection (MOI) of 10. CF neutrophils were isolated from human blood. The human THP-1 monocyte line was also used. THP-1 cells were grown in 10% fetal bovine serum (Thermo scientific) in RPMI. In order to differentiate THP-1 cells into macrophage they were treated with 200 nM PMA (Calbiochem) and 30 ng/mL GM-CSF (R&D Systems, 415-ML-050). Media was replenished with 30 ng/mL GM-CSF the following day and the THP-1 derived macrophages were matured for 5 days before experimentation. THP-1 cells were then treated with the CFTR inhibitor Inh-172 for 24 h prior to experimentation to create CF-like macrophages.

Example 2—AR-13 has Direct Killing Effects on CF Pathogens

In order to determine if AR-12 or its related derivatives had the potential for therapeutic effect against multi-drug resistant pathogens which infect patients with CF, screening was performed for direct killing efficacy against *B. cenocepacia* in media alone. AR-12 and 5 derivative compounds were added to inoculated media for 24 hours and bacterial growth assessed. Only the AR-13 derivative (N-{4-[5-(Phenanthren-2-yl)-3-(trifluoromethyl)-1H-pyrazol-1-yl] phenyl} sulfuric diamide) demonstrated a significant reduction in bacterial growth compared to untreated wells (FIGS. 1A, 1B). Next the synergistic killing of AR-13 with antibiotics against *B. cenocepacia* was assessed. Antibiotics did not enhance direct killing of *B. cenocepacia* in combination with AR-13 (FIG. 1C). Next, AR-13's ability to kill common CF pathogens that can develop antibiotic resistance such as MRSA and *P. aeruginosa* was assessed. AR-13 demonstrated synergistic killing with penicillin/streptomycin and gentamicin against MRSA (FIGS. 1D, 1E). Because synergistic killing was present, a dose-dependent assay was performed and demonstrated the greatest efficacy of AR-13 against MRSA at 5 µM (FIG. 1F). AR-13 did not demonstrate direct killing against *P. aeruginosa* alone, or in combination with antibiotics (FIGS. 1G, 1H).

Example 3—AR-13 Enhances Phagocytic-Mediated Killing in Macrophages from Patients with CF Emerging evidences suggest phagocytic-mediated killing defects in patients with CF contribute to the pathology of infection including virulent multi-drug resistant pathogens such as *B. cenocepacia*. Therefore, we aimed to determine the impact of AR-13 on in-vitro killing of bacteria in the presence of host phagocytes. First, a CFU assay was performed for *B. cenocepacia* growth in human CF and non-CF MDMs. There was no difference in bacterial growth with the addition of AR-13 in CF or non-CF MDMs (FIG. 2A), or with antibiotics alone in CF (FIG. 2B). However, AR-13 demonstrated significant synergistic decreases in *B. cenocepacia* growth in CF MDMs when combined with multiple broad-spectrum gram-negative antibiotics including ceftazidime, ciprofloxacin, gentamicin, and meropenem (FIG. 2B). Next, AR-13 treatment against MRSA in human neutrophils was assessed. AR-13 did not decrease MRSA bacterial load in CF neutrophils, alone or in combination with antibiotics (FIGS. 2C, 2D). Although direct killing of AR-13 against *P. aeruginosa* were not observed, because of the synergistic killing of *B. cenocepacia* in human MDMs, the impact of AR-13 on neutrophil-mediated killing of *P. aeruginosa* was examined because of the known neutrophil role in *Pseudomonas* killing in CF. Both CF and non-CF human neutrophils demonstrated decreased *P. aeruginosa* growth with AR-13 treatment (FIG. 2E). Further synergistic decreases in growth were not noted when CF neutrophils were treated in combination with AR-13 and either ciprofloxacin, gentamicin, or meropenem (FIG. 2F).

Macrophage viability in the presence or absence of AR-13 was conducted to ensure that the observed increase in bacterial killing was not due to decreased cell viability. CF and non-CF macrophages treated with AR-13 alone or in combination with *B. cenocepacia* infection demonstrated no significant differences in cell viability (FIG. 3).

REFERENCES

1. Booth L, Roberts J L, Cruickshanks N, Grant S, Poklepovic A, Dent P. Regulation of OSU03012 toxicity by ER stress proteins and ER stress inducing drugs. Mol Cancer Ther. 2014 October; 13(10):238498. doi: 10.1158/15357163.MCT140172. Epub 2014 Aug. 7. PubMed PMID: 25103559; PubMed Central PMCID: PMC4185238.
2. Chabrier-Rosello Y, Gerik K J, Koselny K, DiDone L, Lodge J K, Krysan D J. *Cryptococcus neoformans* phosphoinositide dependent kinase 1 (PDK1) ortholog is required for stress tolerance and survival in murine phagocytes. Eukaryot Cell. 2013 January; 12(1):1222. doi: 10.1128/EC.0023512. Epub 2012 Oct. 19. PubMed PMID: 23087368; PubMed Central PMCID: PMC3535849.
3. Baxter B K, DiDone L, Ogu D, Schor S, Krysan D J. Identification, in vitro activity and mode of action of phosphoinositidedependent1 kinase inhibitors as antifungal molecules. ACS Chem Biol. 2011 May 20; 6(5): 50210. doi: 10.1021/cb100399x. Epub 2011 Feb. 22. PubMed PMID: 21294551; PubMed Central PMCID: PMC3098953.
4. Chiu H C, Kulp S K, Soni S, Wang D, Gunn J S, Schlesinger L S, Chen C S. Eradication of intracellular *Salmonella enterica* serovar Typhimurium with a small molecule, host cell directed agent. Antimicrob Agents Chemother. 2009 December; 53(12):523644. doi: 10.1128/AAC.0055509. Epub 2009 Oct. 5. PubMed PMID: 19805568; PubMed Central PMCID: PMC2786354.
5. Chiu H C, Yang J, Soni S, Kulp S K, Gunn J S, Schlesinger L S, Chen C S. Pharmacological exploitation of an off target antibacterial effect of the cyclooxygenase2 inhibitor celecoxib against *Francisella tularensis*. Antimicrob Agents Chemother. 2009 July; 53(7):29983002. doi: 10.1128/AAC.000489.

Not every element described herein is required. Indeed, a person of skill in the art will find numerous additional uses of and variations to the methods described herein, which the inventors intend to be limited only by the claims. All references cited herein are incorporated by reference in their entirety.

What is claimed as new and desired to be protected by Letters Patent of the United States is:

1. A method of reducing the load of *Burkholderia cenocepacia* in a host having cystic fibrosis, comprising:

administering (AR-13)

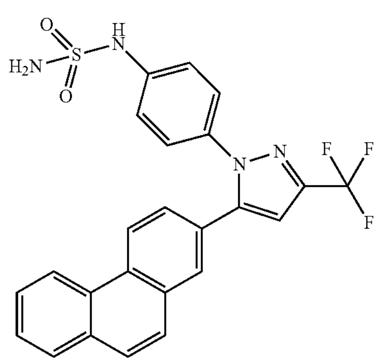 [SMILES: NS(=O)(=O)Nc1ccc(-n2nc(C(F)(F)F)cc2-c2ccc3c(ccc4ccccc43)c2)cc1]

and an antibiotic to the host wherein the load of the microbes is reduced by about 1000 fold.

2. The method of claim 1, wherein the microbes are bacteria.

3. The method of claim 2, wherein the bacteria are multi-drug resistant bacteria.

4. The method of claim 1, wherein the antibiotic is selected from the group consisting of ceftazidime, ciprofloxacin, gentamicin, and meropenem.

5. The method of claim 1, wherein AR-13 is administered to the host in an amount sufficient to achieve a blood or tissue concentration of at least about 2.5 μg/ml.

6. The method of claim 1, wherein the antibiotic is administered to the host in an amount sufficient to achieve a blood or tissue concentration of at least about 5 μg/ml.

7. A method of reducing the titer of *Pseudomonas aeruginosa* in human neutrophils in a host, comprising:

administering (AR-13)

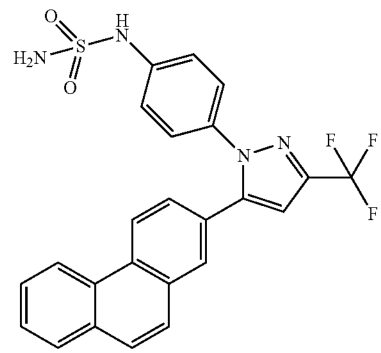

to the host wherein the titer of the *Pseudomonas aeruginosa* in human neutrophils is reduced by at least about 4-10 fold.

8. The method of claim 7, wherein the *Pseudomonas aeruginosa* is antibiotic-resistant.

9. The method of claim 7, wherein AR-13 is administered to the host in an amount sufficient to achieve a blood or tissue concentration of at least about 2.5 μM.

10. The method of claim 7, wherein the antibiotic is administered to the host in an amount sufficient to achieve a blood or tissue concentration of at least about 5 μg/ml.

11. A method of reducing the titer of *Burkholderia cenocepacia* in human CF macrophages, comprising:

administering (AR-13)

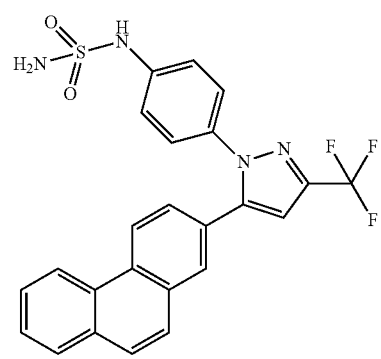

and an antibiotic to the host wherein the titer of the *Burkholderia cenocepacia* in CF macrophages is reduced by about 1000 fold.

12. The method of claim 11, wherein the antibiotic is selected from the group consisting of ceftazidime, ciprofloxacin, gentamicin, and meropenem.

13. The method of claim 11, wherein AR-13 is administered to the host in an amount sufficient to achieve a blood or tissue concentration of at least about 2.5 μM.

14. The method of claim 11, wherein the antibiotic is administered to the host in an amount sufficient to achieve a peak blood or tissue concentration of at least about 5 μg/ml.

* * * * *